United States Patent
Klingler et al.

(12)

(10) Patent No.: US 6,218,575 B1
(45) Date of Patent: Apr. 17, 2001

(54) PROCESS FOR PREPARING ADRENALINE

(75) Inventors: Franz Dietrich Klingler, Griesheim; Lienhard Wolter, Hochstetten/Dhaun, both of (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/625,881

(22) Filed: Jul. 26, 2000

(30) Foreign Application Priority Data

Aug. 14, 1999 (DE) .............................. 199 38 709

(51) Int. Cl.[7] .................................. C07C 209/00
(52) U.S. Cl. ............................. 564/358; 564/304
(58) Field of Search .................... 564/304, 358

(56) References Cited

PUBLICATIONS

Achiwat et al Tetrahedron Letters 30 (1989), 367–370.*
Chem. Pharm. Bull. 43 (5) (1995) 738–747.*
Tetrahedron Letters 5 (1979), 425–428.*

\* cited by examiner

*Primary Examiner*—Samuel Barts
(74) *Attorney, Agent, or Firm*—R. P. Raymond; T. X. Witkowski

(57) ABSTRACT

An improved process for preparing adrenaline, or an addition salt thereof, on an industrial scale, with asymmetric hydrogenation as a key step and a special sequence of successive steps, using $[Rh(COD)Cl]_2$ as catalyst and a chiral, bidentate phosphine ligand such as (2R,4R)-4-(dicyclohexylphosphino)-2-(diphenylphosphinomethyl)-N-methylaminocarbonylpyrrolidine as the catalyst system.

19 Claims, No Drawings

PROCESS FOR PREPARING ADRENALINE

The present invention relates to an improved process for preparing adrenaline, or an addition salt thereof, on an industrial scale, with asymmetric hydrogenation as a key step and a special sequence of successive steps, using [Rh(COD)Cl]$_2$ as catalyst and a chiral, bidentate phosphine ligand such as (2R,4R)-4-(dicyclohexylphosphino)-2-(diphenylphosphinomethyl)-N-methylaminocarbonylpyrrolidine as the catalyst system.

BACKGROUND OF THE INVENTION

Adrenaline is a hormone and neurotransmitter which belongs to the catecholamines. In the human body, it is formed from tyrosine when the latter is reacted via dihydroxyphenylalanine, dopamine, and noradrenaline, finally producing adrenaline. Adrenaline, being a sympathetic agent, stimulates the adrenergic receptors of the sympathetic nervous system, increasing the pulse rate, cardiac output, and systolic blood pressure, reducing intestinal peristalsis, relaxing the bronchial muscles and dilating the bronchi, dilating the pupils, increasing the basal metabolic rate by promoting O$_2$ consumption, hyperglycemia and glycosuria by mobilizing the glycogen reserves in the liver and increasing lipolysis, inter alia, thereby increasing the free fatty acids in the blood. Because of its wide range of activities adrenaline is of considerable commercial interest in the treatment of anaphylactic shock, inter alia, or as an addition to local anesthetics.

Chemically, adrenaline is L-1-(3',4'-dihydroxyphenyl)-2-methylaminoethan-1-ol with the following structure (Formula I):

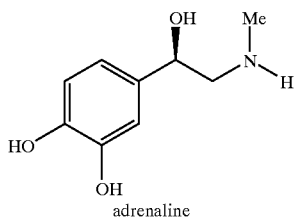

adrenaline

PRIOR ART

Industrially, adrenaline is usually manufactured by non-stereoselective hydrogenation of 3',4'-dihydroxy-2-N-methylaminoacetophenone or a derivative thereof with protected OH functions or amino function and subsequent racemate separation.

Enantioselective methods of synthesis are also known. One of these is described, for example, in Tetrahedron Letters 5 (1979), 425–428. According to this method, 3',4'-dihydroxy-2-N-methylaminoacetophenone is reacted to produce adrenaline by hydrogenation under a hydrogen pressure of about 50 bar using a chiral hydroxyalkylferrocenylphosphine as catalyst. The amount of catalyst to substrate is about 1:100, based on the molar ratio. Under these conditions, L-1-(3',4'-dihydroxyphenyl)-2-methylaminoethan-1-ol (adrenaline) is obtained in an enantiomeric excess over the S-enantiomer of 60% ee after about 2 to 4 days reaction.

This process, however, is unsuitable for producing adrenaline on an industrial scale for a number of reasons: in spite of the use of large amounts of catalyst in the asymmetric reaction step, the product cannot be produced in sufficiently pure form for pharmaceutical purposes except by the use of expensive purification procedures, as this reaction produces adrenaline only as a mixture containing a relatively high proportion of the opposite enantiomer as a contaminant. The relatively long reaction time of the asymmetric hydrogenation step, i.e., 2 to 4 days, also constitutes a reaction step which is very equipment-intensive and expensive for industrial purposes, with not inconsiderable safety risks.

Achiwa et al., writing in Tetrahedron Letters 30 (1989), 367–370 and Chem. Pharm. Bull. 43 (5) (1995) 738–747, describe an asymmetric rhodium catalyst which was used in the manufacture of L-phenylephrine. Using asymmetric hydrogenation, 3'-benzyloxy-2-(N-benzyl-N-methyl) aminoacetophenone hydrochloride is reduced within 20 hours with hydrogen in the presence of [Rh(COD)Cl]$_2$/(2R,4R)-4-(dicyclohexylphosphino)-2-(diphenylphosphinomethyl)-N-methylaminopyrrolidine as catalyst. After filtration, concentration of the reaction mixture and cleaving of the benzyl nitrogen protecting group, phenylephrine is obtained as the product. In addition to the L-enantiomer, the D-enantiomer is also obtained in an amount of at least 7.5% as a contaminant (85% ee). The precise mechanism of rhodium-catalyzed asymmetric hydrogenation is not known at present.

The main disadvantage of this process is that the L-phenylephrine obtained cannot be purified economically on an industrial scale to the level of purity essential for its use as a pharmaceutical. Moreover, the hydrogenation reaction is relatively long, taking more than 20 hours, which is associated with the disadvantages described above.

It is not known to produce adrenaline by this method.

SUMMARY OF THE INVENTION

The present invention relates to a new process for preparing adrenaline by asymmetric hydrogenation which overcomes the problems and drawbacks known from the prior art or described above.

One of the essential objectives of the present invention is to develop a process by mean., of which adrenaline can be produced with high optical and chemical purity. Thus, for example, the risk of the unwanted enantiomer contaminating pharmaceutical preparations which contain adrenaline as active ingredient should be minimized.

Another objective of the invention is to develop a process by means of which substantially enantiomerically pure adrenaline can be produced easily, i.e., without complicated purification procedures.

A further aim of the invention is to produce adrenaline by means of a stereoselective process in order to avoid reaction steps in which chiral intermediate compounds or the chiral end product adrenaline is obtained as a racemate together with its opposite enantiomer in a similar amount.

The process according to the invention also sets out to keep the hydrogenation times needed for adrenaline production as short as possible in order to reduce the costs and risks involved in using hydrogen under high pressure, inter alia.

Another aim of the present invention is to provide the skilled person with a process for manufacturing adrenaline by which this substance, which is needed in large quantities, can be produced cheaply from readily available educts.

Surprisingly, it has now been found that adrenaline or the sulphate thereof can be obtained in exceptionally high optical purity from 3',4'-dihydroxy-2-N-benzyl]-N-methylaminoacetophenone 1 using asymmetric hydrogenation with [Rh(COD)Cl]$_2$/(2R,4R)-4-dicyclohexylphosphino)-2-(diphenylphosphinomethyl)-N-methylaminocarbonylpyrrolidine (RR-MCCPM) as the catalyst system and a special sequence of subsequent steps. The abbreviation COD used in the general formula denotes cyclooctadiene.

DETAILED DESCRIPTION OF THE INVENTION

With a molar ratio of catalyst to substrate of about 1:1500 (see Example), adrenaline sulphate 3 can be obtained by the process according to the invention, starting from benzyladrenalone (3',4'-dihydroxy-2-N-benzyl-N-methylaminoacetophenone) 1, with an optical purity of 98% ee or more (HPLC) (reaction diagram 1).

Reaction diagram 1:

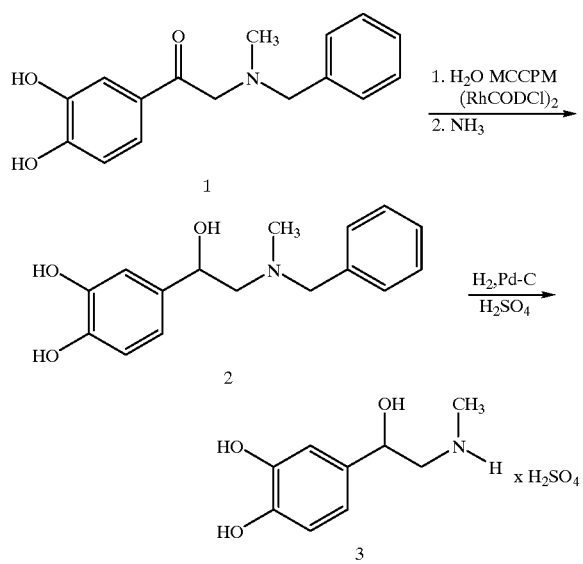

According to reaction diagram 1, first of all 3',4'-dihydroxy-2-N-benzyl-N-methylaminoacetophenone 1 is reacted by asymmetric hydrogenation, using [RH(COD)Cl]$_2$/(2R,4R)4-(dicyclohexylphosphino)-2-(diphenylphosphinomethyl)-N-methylaminopyrrolidine as catalyst, to form the optically active benzyladrenaline base (R-1-(3',4'-dihydroxyphenyl)-2-N-benzyl-N-methylaminoethan-1-ol) 2 (reaction step 1). This is then precipitated in the basic range by the addition of ammonia (reaction step 2). In a 3rd reaction step the benzyl protecting group is then eliminated by hydrogenation with hydrogen and palladium, preferably palladium on charcoal, in a sulfuric acid solution, so as to obtain the adrenaline sulphate 3.

For easy production of almost optically pure adrenaline or its sulphate 3, another important step, in addition to asymmetric hydrogenation with the rhodium catalyst described above, is precipitation of the N-benzyladrenaline 2. By means of these two steps taken together, asymmetric hydrogenation plus precipitation of the benzyladrenaline in the basic range, an intermediate compound with high optical purity is readily obtained, from which adrenaline or the acid addition salts thereof can be obtained with high optical purity in another simple reaction step.

The educt 1 may be, apart from 3',4'-dihydroxy-2-N-benzyl-N-methylaminoacetophenone, another derivative of 3',4'-dihydroxy-2-N-methylaminoacetophenone (adrenalone), in which the nitrogen function either has no further protection, is protected as a salt or is protected with a protecting group other than the benzyl protecting group. Suitable protecting groups of this kind include, for example, tert-butylcarbonyl-, 9-fluorenylmethylcarbonyl- or another nitrogen protecting group known from the relevant prior art. N-protected 1-(3',4'-dihydroxy)-2-N-methylaminoacetophenone derivatives having a protecting group which is stable under the reaction conditions of the first reaction step (asymmetric hydrogenation) are preferred. 3',4'-dihydroxy-2-N-benzyl-N-methylaminoacetophenone 1 is particularly preferred as the educt. The free base 1 or an addition salt thereof, for example, with an organic acid, can be used as the educt.

The catalyst used according to the invention is [Rh(COD)Cl]$_2$ and a chiral, bidentate phosphine ligand. Preferably, (2R,4R)-4-(dicyclohexylphosphino)-2-(diphenylphosphinomethyl)-N-methyl-aminocarbonylpyrrolidine (RR-MCCPM) is used as catalyst.

The preparation of this catalyst is known from the prior art [EP-A-0 251 164, EP-A-O 336 123]. According to the invention, the catalyst may also be present in polymer-bound form, e.g., with the chiral ligand (2R,4R)4-dicyclohexylphosphino)-2-(diphenylphosphinomethyl)-N-methylaminocarbonyl) pyrrolidine being bound to a polymer via the phenyl groups. The use of polymer-bound ligands of this kind does not necessarily rule out the use of non-polymer-bound ligands at the same time. Polymer-bound catalysts of this kind are particularly advantageous for easy purification of the product.

The catalyst is used either as a pre-prepared, oxygen-free solution of [Rh(COD)Cl]$_2$ and ligand or prepared in situ from [Rh(COD)Cl]$_2$ and ligand in the presence of the 3',4'-dihydroxy-2-N-benzyl-N-methylaminoacetophenone 1 without oxygen, under a protective gas atmosphere or hydrogen atmosphere.

The molar ratio of educt 1 to catalyst in the process according to the invention is between 500:1 and 10,000:1; generally between 500:1 and 3000:1; preferably between 500:1 and 2000:1; more preferably between 1000:1 and 2000:1; preferably about 1000:1; and most preferably about 1500:1.

The reaction medium used for the first reaction step (asymmetric hydrogenation with the rhodium catalyst) is a protic solvent which is preferably degassed before use. A $C_1$ to $C_3$-alcohol, namely methanol, ethanol, propanol, or isopropanol, is preferred, especially methanol or ethanol, most preferably methanol. The solvent may optionally contain water.

The reaction temperature of this first step is preferably between 40 and 70° C., most preferably 45 to 55° C.

The hydrogen pressure is 10 to 100 bar, preferably 10 to 50 bar and more preferably 15 to 25 bar.

This first reaction step is complete after 2 to 8 hours, preferably 4 to 6 hours.

Then the solvent is evaporated down sharply by distillation, optionally diluted with water and active charcoal is added thereto. After the active charcoal has been filtered off again, the reaction mixture is diluted with water and preferably the same solvent that was used for the asymmetric hydrogenation, and a base is added in order to precipitate out the N-benzyladrenaline (L-1-(3',4'-dihydroxyphenyl)-2-N-benzyl-N-methylaminoethan- 1-ol) 2 in high optical yields.

Suitable bases are weak organic or inorganic bases. In both cases nitrogen bases are particularly preferred. Of the organic bases, nitrogen bases such as pyridine, piperidine, triethylamine, diethylamine, ethyl-isopropylamine, methylamine, or derivatives thereof are particularly preferred, provided that they are soluble in the solvent. Ammonia is particularly preferred among the inorganic bases. Ammonia is particularly preferred.

The substantially enantiomerically pure N-benzyladrenaline 2 obtained is hydrogenated with hydrogen in a third step. A palladium catalyst is preferably used, especially palladium on charcoal. This hydrogenation preferably takes place in the acid range. The pH of the solution is adjusted to 4 to 6, more preferably 5 to 6, by the addition of acid.

The solvent for this reaction step is water, a $C_1$ to $C_3$-alcohol, namely methanol, ethanol, propanol, or isopropanol or a mixture thereof Water, water-methanol mixtures, or methanol are preferred. Water is particularly preferred.

Inorganic or organic acids may be used to acidify the solution. Examples of organic acids include: formic acid, acetic acid, propanoic acid, tartaric acid, malic acid, succinic acid, and citric acid. Examples of inorganic acids include: sulfuric acid, hydrochloric acid and phosphoric acid. Sulfuric acid is preferred.

The reaction temperature for this reaction step is between 40 and 80° C., preferably between 50 and 70° C. and is most preferably 60° C.

The hydrogen pressure is 1 to 5 bar, preferably 2 to 3 bar.

Using the process according to the invention, adrenaline can be obtained by means of all three reaction steps in a total yield of 75% or more, with an optical purity of 98% ee or more and a chemical purity of 98% or more.

The advantage of the process according to the invention is that the amount of catalyst can be significantly reduced in relation to comparable methods known from the prior art, or the reaction time of the asymmetric hydrogenation can be substantially reduced whilst at the same time achieving an increase in the optical yield.

In addition, the process according to the invention makes it possible to carry out optical purification at the stage of the intermediate product, N-benzyladrenaline 2, and thereby easily obtain adrenaline of high optical purity.

The process according to the invention will now be illustrated by the following Example. This Example serves only as an illustration and is not to be regarded as limiting.

EXAMPLE

Preparation of the catalyst solution 6 mg of dichlorobis[(cycloocta-1,5-diene)rhodium (I)] and 8.2 mg of RR-MCCPM (2R,4R)-4-(dicyclohexylphosphino)-2-(diphenylphosphinomethyl)-N-methylaminocarbonylpyrrolidine) are added to 10 ml of degassed methanol under protective gas and stirred for 30 minutes at ambient temperature.

Preparation of adrenaline 7.4 g of the hydrochloride of benzyladrenalone 1 are dissolved in about 60 ml of methanol (degassed), 0.07 ml of triethylamine and 10 ml of the catalyst solution (corresponding to 6 mg of $(RhCODCl)_2$ and 8.2 mg of RR-MCCPM) are added and the mixture is hydrogenated at about 50° C. under about 20 bar of hydrogen pressure. After the reaction has ended the methanol is largely distilled off, about 30 ml of water and about 0.5 g of active charcoal are added, the mixture is stirred for 30 minutes and filtered. Then N-benzyladrenaline 2 is precipitated with about 10 ml of water and about 15 ml of methanol and by adding about 4 ml of ammonia (about 25% strength) and then filtered off. (R.T.) Yield 6 g=90%.

Benzyladrenaline 2 is dissolved in about 10 ml of water and about 5 ml of 18% sulfuric acid (pH: about 5.5), about 50 mg of palladium-charcoal (10%) are added and the mixture is hydrogenated at about 60° C. under 2 bar of hydrogen pressure. It is then evaporated down to about half its volume, about 20 ml of methanol are added and the mixture is cooled. The crystalline product (adrenaline sulphate 3) is filtered off and dried.

Yield over all the steps taken together: about 4.5 g (about 75%) optical purity:>98% ee (HPLC) chemical purity:>98% (HPLC).

We claim:

1. A method for preparing adrenaline or an addition salt of adrenaline from an N-protected adrenalone, comprising:

(a) subjecting the N-protected adrenalone to asymmetric hydrogenation with $[Rh(COD)Cl]_2$ and a chiral, bidentate phosphine ligand as a catalyst system to obtain an N-protected adrenaline;

(b) precipitating the N-protected adrenaline in the basic range; and (c) cleaving the N-protecting group of the precipitated N-protected adrenaline in the acid range to obtain adrenaline or an addition salt of adrenaline.

2. The method according to claim 1, wherein the N-protected adrenalone is N-benzyladrenalone and the N-protected adrenaline is N-benzyladrenaline.

3. The method according to claim 2, wherein in step (c) the benzyl nitrogen protecting group of the N-benzyladrenaline is cleaved by hydrogenation in the presence of a palladium catalyst.

4. The method according to one of claims 1 or 2, wherein the phosphine ligand is (2R,4R)-4-(dicyclohexylphosphino)-2-(diphenylphosphinomethyl)-N-methylaminocarbonylpyrrolidine.

5. The method according to one of claims 1 or 2, wherein the phosphine ligand is polymer-bound (2R,4R)-4-(dicyclohexylphosphino)-2-(diphenylphosphinomethyl)-N-methylaminocarbonylpyrrolidine.

6. The method according to one of claims 1 or 2, wherein the asymmetric hydrogenation is carried out in a temperature range from 40° C. to 70° C.

7. The method according to one of claims 1 or 2, wherein the asymmetric hydrogenation is carried out under a pressure of 10 bar to 100 bar.

8. The method according to one of claims 1 or 2, wherein the asymmetric hydrogenation is carried out in a protic solvent.

9. The method according to claim 8, wherein the asymmetric hydrogenation is carried out in a solvent selected from the group consisting of: methanol, ethanol, propanol, and isopropanol.

10. The method according to claim 9, wherein the solvent for the asymmetric hydrogenation contains water.

11. The method according to one of the claims 1 or 2, wherein the molar ratio of the N-protected adrenalone to the $[Rh(COD)Cl]_2$ in the asymmetric hydrogenation is between 500:1 and 10000:1.

12. The method according to one of claims 1 or 2, wherein the molar ratio of the N-protected adrenalone to the $[Rh(COD)Cl]_2$ in the asymmetric hydrogenation is between 500:1 and 3000:1.

13. The method according to one of claims 1 or 2, wherein the molar ratio of the N-protected adrenalone to the $[Rh(COD)Cl]_2$ in the asymmetric hydrogenation is between 1000:1 and 2000:1.

14. The method according to one of the claims 1 or 2, wherein the [Rh(COD)Cl]$_2$ for the asymmetric hydrogenation is used as a pre-prepared solution.

15. The method according to one of the claims 1 or 2, wherein the [Rh(COD)Cl]$_2$ for the asymmetric hydrogenation is produced in situ.

16. The method according to one of claims 1 or 2, wherein in step (b) a nitrogen base is used as the base for precipitating the N-protected adrenaline.

17. The method according to one of claims 1 or 2, wherein in step (c) sulfuric acid, hydrochloric acid, or phosphoric acid is used to acidify the solvent.

18. The method according to one of claims 1 or 2, wherein the pH of step (c) is between 5 and 6.

19. The method according to one of claims 1 or 2, wherein the reaction temperature of the step (c) is 40 to 80° C.

* * * * *